United States Patent [19]
Che

[11] Patent Number: 6,140,653
[45] Date of Patent: Oct. 31, 2000

[54] LARGE-FIELD FLUORESCENCE IMAGING APPARATUS

[75] Inventor: Diping Che, Westmont, Ill.

[73] Assignee: Vysis, Inc., Downers Grove, Ill.

[21] Appl. No.: 09/049,748

[22] Filed: Mar. 27, 1998

[51] Int. Cl.[7] .................................................. G01N 21/64
[52] U.S. Cl. ......................................................... 250/458.1
[58] Field of Search ........................................ 250/458.1

[56] References Cited

U.S. PATENT DOCUMENTS

| | | |
|---|---|---|
| 4,022,529 | 5/1977 | White ...................................... 356/318 |
| 4,419,583 | 12/1983 | Noeller . |
| 4,451,149 | 5/1984 | Noeller . |
| 4,555,177 | 11/1985 | Barrett . |
| 4,859,063 | 8/1989 | Fay et al. . |
| 5,162,654 | 11/1992 | Kostichka et al. . |
| 5,247,318 | 9/1993 | Suzuki . |
| 5,377,003 | 12/1994 | Lewis et al. . |
| 5,422,719 | 6/1995 | Goldstein . |
| 5,500,536 | 3/1996 | Nogami et al. . |
| 5,528,368 | 6/1996 | Lewis et al. . |
| 5,557,415 | 9/1996 | Nielsen et al. . |
| 5,563,417 | 10/1996 | Gillard et al. . |
| 5,578,832 | 11/1996 | Trulson et al. . |
| 5,585,639 | 12/1996 | Dorsel et al. . |
| 5,646,411 | 7/1997 | Kain et al. . |
| 5,672,880 | 9/1997 | Kain . |
| 5,719,391 | 2/1998 | Kain . |
| 5,793,049 | 8/1998 | Ballard ................................. 250/458.1 |

FOREIGN PATENT DOCUMENTS

| | | |
|---|---|---|
| 0 340 915 A2 | 11/1989 | European Pat. Off. . |
| 0 674 160 A1 | 9/1995 | European Pat. Off. . |
| 1427252 A1 | 9/1988 | U.S.S.R. ............................. 250/458.1 |
| WO 94/24529 | 10/1994 | WIPO . |
| WO 96/05488 | 2/1996 | WIPO . |

*Primary Examiner*—Constantine Hannaher
*Attorney, Agent, or Firm*—Norval B. Galloway

[57] ABSTRACT

A large-field fluorescence imaging apparatus couples an excitation beam produced by a high-power white light source to a sample with reflective optics to achieve high illumination intensity on the sample. The reflective optics includes a concave mirror which projects the filtered and collimated excitation beam from the white light source onto the sample surface. The concave mirror images a field stop onto the sample surface to define an illumination area which matches the field of view of the imaging optics. The fluorescent light generated in the sample is filtered and imaged on a charge coupled device. The combination of the high illumination intensity and the imaging efficiency allows the imaging apparatus to acquire fluorescent images at an improved rate. A sample-height alignment arrangement using fixed alignment stops allows the sample to be positioned quickly and repeatably in the focal plane of the imaging optics without the need for fine adjustments.

17 Claims, 2 Drawing Sheets

LARGE-FIELD FLUORESCENCE IMAGING APPARATUS

FIELD OF THE INVENTION

This invention relates generally to fluorescent light excitation and detection, and more particularly to an apparatus for collecting a large-field fluorescent image of a sample under study.

BACKGROUND OF THE INVENTION

Fluorescence imaging techniques have been widely used in studying biological samples and the like. To take a fluorescent image of a sample, the sample is illuminated with an excitation light beam which has an frequency band selected for exciting certain fluorophors in the sample. The fluorescent light generated by the excited fluorophors is then collected by light detectors to form an image of the sample.

Based on the type of light source used for generating the excitation light, existing fluorescence imaging devices can be generally divided into laser-based and white light-based devices. A laser-based fluorescence imaging device uses a laser as the light source. There are several disadvantages associated with a laser-based imaging device. A laser generally provides only one or at most a few usable frequencies for fluorescence excitation and therefore does not provide flexibility in the selection of excitation frequency. Moreover, the application of lasers for fluorescence excitation is relatively expensive.

A white light-based fluorescence imaging device uses a light source that generates light over a broad frequency spectrum. The broad-band light (which is typically called white light or polychromatic light) from the light source is filtered to provide excitation light within a narrow band around a selected excitation frequency. The light generated by the white light source is typically transmitted to the sample via an optical fiber bundle. Due to the high numerical aperture of the optical fiber bundle, the excitation beam tends to be highly divergent, resulting in a low illumination intensity on the sample. Another significant disadvantage of such a lighting arrangement is that the imaging system tends to be fairly bulky and less suitable for field applications.

The amount of time required to take a fluorescent image is a critical performance parameter of a fluorescence imaging device. To improve the image acquisition rate, both the efficiency of sample illumination and the efficiency of fluorescent light detection have to be maximized. A high image acquisition rate is especially difficult to achieve when a relatively large area on the sample (typically on the order of one square centimeter) is to be imaged. Some existing laser-based imaging devices focus the input laser beam into a small spot which is scanned across the sample surface to obtain a fluorescent image of the sample. Such a device, for example, is shown in U.S. Pat. No. 5,672,880 to Kain. The disadvantages of an imaging device using a scanning laser beam includes the long scanning time required for acquiring one image and the complexity and costs of the scanning mechanism.

SUMMARY OF THE INVENTION

In view of the foregoing, it is a general object of the invention to provide a large-field fluorescence imaging apparatus that provides high quality large-field images with reduced image acquisition time than heretofore achievable with known prior art devices.

It is a related object of the invention to provide a large-field fluorescence imaging apparatus that provides flexibility in excitation frequency selection and has an optical configuration that is robust, reliable, highly efficient, compact, and can be constructed at a relatively low cost.

In accordance with these and other objects of the invention, there is provided a large-field fluorescence imaging apparatus which uses reflective optics to couple the excitation beam generated by a high-power white light source onto the sample surface to provide a high illumination intensity, and combines the high illumination intensity with the high detection efficiency of an array detector to provide a high image acquisition rate. The white light generated by the light source is collimated and filtered to provide the excitation beam. The excitation beam is passed through a field stop to form a well defined beam pattern and then projected onto the sample surface with a concave mirror. The concave mirror is disposed to image the field stop on the sample to define an illumination area which matches the field of view of the imaging optics. The fluorescent light generated in the sample is filtered and imaged by the imaging optics onto the array detector to produce a fluorescent image of the sample.

Other objects and advantages will become apparent with reference to the following detailed description when taken in conjunction with the drawings in which:

Figure 1:
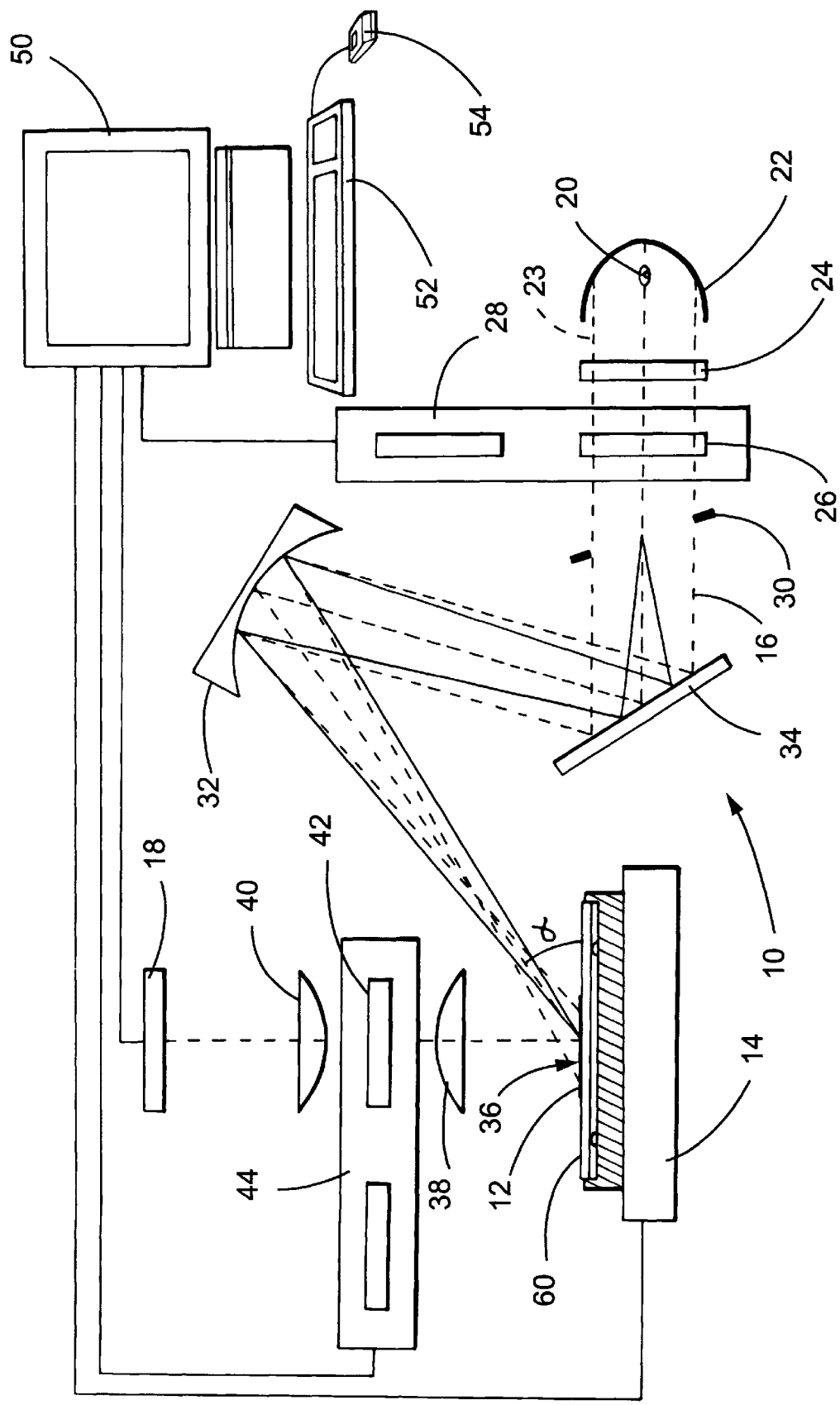
FIG. 1 is a schematic diagram showing the optical components of an embodiment of the large-field fluorescence imaging apparatus of the invention.

While the invention is susceptible of various modifications and alternative constructions, certain illustrated embodiments hereof have been shown in the drawings and will be described below. It should be understood, however, that there is no intention to limit the invention to the specific forms disclosed, but, on the contrary, the intention is to cover all modifications, alternative constructions and equivalents falling within the spirit and scope of the invention as defined by the appended claims.

DETAILED DESCRIPTION OF THE PREFERRED EMBODIMENT

Turning now to the drawings, FIG. 1 shows an embodiment of a large-field fluorescence imaging apparatus 10 constructed according to the invention. A sample 12 to be studied is mounted on a support stage 14 under imaging optics. In accordance with an aspect of the invention, a relatively large area (on the order of one square centimeter or more) of the sample 12 is illuminated by an excitation beam 16 to excite fluorescent transactions in the sample. The fluorescent light from the illuminated sample is collected by an array detector 18 to generate a fluorescent image of the sample.

The excitation beam 16 is generated by a high-power white light source 20 which produces light over a broad spectrum. As used herein, the term "white light" describes light which covers a broad spectrum over the visible light range. The frequency distribution of the white light does not have to be uniform or continuous, and the light is not necessarily white in color by human perception. The white light is also commonly referred to as "polychromatic." The white light generated by the light source 20 is collimated into a white light beam 23 by a reflector 22.

In one implementation of the embodiment, the light source 20 is a xenon arc lamp which produces light upon application of electrical current and has an output power of 175 watt or higher. The reflector 22 for collimating the white light generated by the arc lamp is a parabolic mirror. The arc lamp and the parabolic mirror are available as an assembly from, for example, ILC Technology Corp. in Sunnyvale, Calif. as Model LX175.

The use of a white light source 20 has many advantages. A white light source is readily available and costs significantly less than a laser. The high power of a white light source provides improved sample illumination intensity which shortens the image acquisition time. As another significant advantage, the broad spectrum of the white light allows the same light source to be used to provide light in different excitation frequency bands for many kinds of fluorophors.

The white light beam 23 as collimated by the reflector 22 is passed through a "hot mirror" 24, which allows light with energies usable for fluorescence excitation to pass while blocking the infrared portion of the white light to prevent heating of the downstream optical components and the sample. In an implementation of the embodiment, the hot mirror 24 is a heat-resistant glass plate with dielectric coating, which is available, for example, as Model A200HMP from ILC Technology Corp. The light beam filtered by the hot mirror 24 then passes through an input filter 26 to form the excitation light beam 16 within a selected frequency band for exciting a specific fluorophor in the sample 12. The filter 26 preferably has a relatively narrow pass bandwidth, typically on the order of 20 nm, and a relatively large size, on the order of one square inch. Such filters are available, for example, from Chroma Technology, Inc. in Brattleboro, Vt.

In the preferred embodiment of FIG. 1, a plurality of input filters with different pass bands for exciting different fluorophors are mounted on a filter wheel 28. Which filter is used for fluorescence imaging depends on the fluorophors in the sample. The selection of a filter on the filter wheel 28 with a desired excitation frequency band is accomplished by rotating the filter wheel to a specific orientation to put the selected filter in the path of the light beam. The excitation beam 16 from the filter 26 is then passed through the opening of a field stop 30. The field stop 30 is used to block the fringe portion the excitation beam 16 to form a well-defined beam pattern which is projected onto the sample 12 to define an illumination area.

In accordance with a feature of the invention, the excitation light generated by the white light source is directly coupled to the sample surface with a very simple and efficient reflective optical arrangement. The reflective optics includes a concave mirror 32 which projects the excitation beam 16 onto the sample surface for large-field illumination. In an implementation of the embodiment of FIG. 1, the concave mirror 32 is a spherical mirror about two inches in diameter and having a curvature radius of 250 mm. The excitation beam from the input filter 26 is reflected by a flat mirror 34 which redirects the excitation beam to the concave mirror 32. The concave mirror 32 in turn projects the excitation beam onto the upward-facing surface of the sample 12 at an acute incident angle. The concave mirror 32 is positioned to image the field stop 30 on the sample 12 to form a well-defined illumination area 36. The illumination area is preferably slightly larger than the field of view of the imaging optics, but may be adjusted to any desirable size by adjusting the opening of the field stop 30. The incident angle of the excitation beam 16 on the concave mirror 32 should be small enough so that the distortion of the image of the field stop 30 on the sample is acceptable. On the other hand, the incident angle should be sufficiently large so that the light reflected by the concave mirror 32 will not be blocked by the flat mirror 34.

It should be noted that in the illustrated embodiment the flat mirror 34 is used mainly for redirecting the horizontal excitation beam from the light source to the concave mirror 32. The initial direction of the excitation beam 16 is determined by the orientation of the light source 20 and the reflector 22. If the light source 20 and reflector 22 are positioned to generate a generally vertical beam which can be aimed directly at the concave mirror 32, the flat mirror 34 will not be needed.

The use of the reflective optics to project the excitation beam 16 onto the sample 12 has multiple advantages. It simplifies the optical configuration and improves the efficiency of the system by reducing the number of surfaces in the path where reflective losses occur. It avoids the need to use an optical fiber bundle or the like to bring the input light to a point close to the sample for illumination thereof. This allows the imaging apparatus to have a compact size and a robust structure suitable for field applications. In one implementation of the embodiment, the imaging apparatus can be fitted in a housing of 14" H×6.5" W×23" D. Furthermore, the use of reflective optics avoids transmission losses and chromatic imperfections associated with lenses, fiber optics, and refractive optics. This is especially important in applications where fluorescent images of more than one color are to be acquired. Another advantage of using the reflective optics is that it avoids passing the excitation light through any optical component, such as a lens or a prism, which tends to generate autofluorescence.

In the preferred embodiment, the field stop 30 is tilted away from being perpendicular to the optical axis of the reflector 22, the hot mirror 24, and the input filter 26 by a small angle. This arrangement allows the edges of the opening of the field stop 30 to be sharply focused on the sample 12 by the concave mirror 32. By defining the illumination area 36 to closely match the field of view of the imaging optics, the amount of stray light and background fluorescence into the imaging optics is reduced.

The imaging optics collects the fluorescent light emitted by excited fluorophors in the sample and images the fluorescent light onto the array detector 18. In the embodiment of FIG. 1, the imaging optics includes a pair of imaging lenses 38 and 40. By way of an analogy with a microscope, the first imaging lens 38 functions as an infinity corrected objective, and the second imaging lens 40 functions as a tube lens. Each of the imaging lenses preferably has a high numerical aperture, large field of view, and small aberration. In an implementation of the embodiment, the lenses are 50 mm F/1.2 camera lenses made by Nikon Corp.

In the preferred embodiment, the optical axes of the imaging lenses 38 and 40 are aligned with each other and perpendicular to the sample surface. The excitation beam 16 reflected by the concave mirror 32 is directed to illuminate the surface of the sample 12 at an acute angle α, and the excitation beam is reflected from the sample about an angle of (180°—α). This illumination/collection geometry prevents the reflected excitation beam from passing through the collection lenses 38 and 40, thereby avoiding generating background fluorescent light in the imaging lenses. The working distance of the imaging lens 38 should be sufficiently large so that it does not block the incident excitation beam from the concave mirror 32.

An output filter 42, which is placed between the imaging lenses 38 and 40 in the illustrated embodiment, allows the fluorescent light from the sample to pass but blocks any excitation light reflected or scattered by the sample and other unwanted light from the sample. The sample surface is located at the focal point of the lens 38 so that the fluorescent light collected by the lens 38 is collimated to accommodate the small acceptance angle of the output filter 42. This arrangement reduces the focusing problem due to filter change.

The size of the output filter 42 should be sufficiently large to accept the fluorescent light collimated by the first lens 38. In one implementation, the output filter 42 has a diameter of about 2 inches. In the preferred embodiment, the output filter 42 has a plurality of pass bands for fluorescent light. Thus, the same output filter can be used for taking fluorescent images of different colors. Filters with multiple pass bands are available, for example, from Chroma Technology, Inc. The output filter 42 in the illustrated embodiment is mounted on a filter wheel 44, which supports multiple output filters selectable by rotating the filter wheel to place the desired filter in the path of the fluorescent light.

The array detector 18 for collecting the fluorescent image of the sample 12 is positioned at the focal point of the imaging lens 40. The image magnification is determined by the ratio of the effective focal lengths of the lenses 38 and 40. In the preferred embodiment, the array detector 18 is a charge-coupled device (CCD) with a large grid of pixels. The balance between the size of the view field and the image resolution is obtained by choosing the CCD pixel size, the total CCD imaging area, and image magnification.

The use of the imaging optics with an array detector 18 allows the acquisition of an image with a relatively large field of view, on the order of several square centimeters. The combination of the high illumination intensity on the sample and the multi-channel detection of the array detector significantly reduces the image acquisition time. It also eliminates the necessity of accurate positioning mechanism required by prior art imaging devices that use a scanning laser beam.

In the preferred embodiment, the operations of the input filter wheel 28, the output filter wheel 44, and the positioning of the sample stage 14 are controlled by a computer 50. The computer 50 is further connected to the charge coupled device 18 for receiving and analyzing fluorescent light intensity data collected thereby. The user uses an input device, such as the keyboard 52 or the mouse 54, to specify the input and output filters to be used in the image acquisition and the position of the sample for imaging. The computer then rotates the input filter wheel and the output filter wheel to move the selected input and output filters into their respective operation positions. The computer also controls the movement of the sample stage 14 in X, Y, and Z directions.

Figure 2:
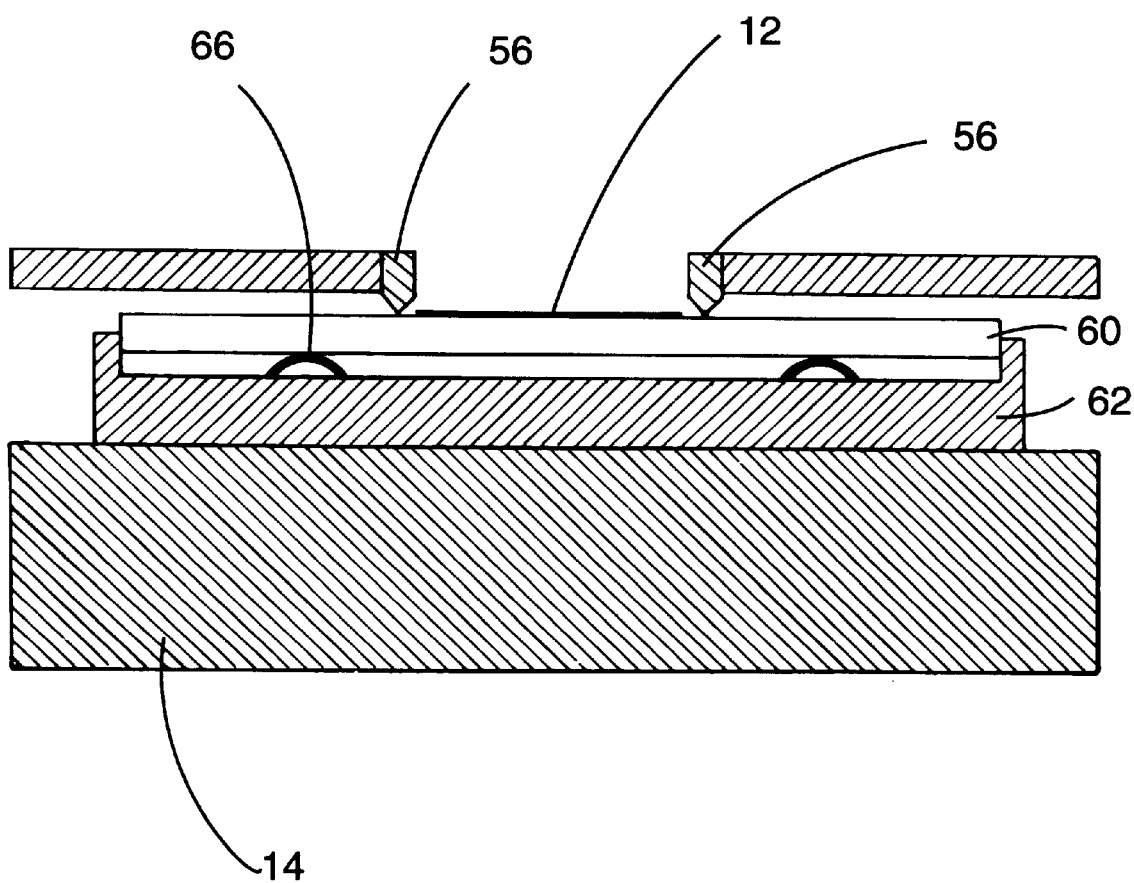
FIG. 2 is a schematic diagram showing a sample mounting and positioning arrangement.

In accordance with a feature of the preferred embodiment, the positioning of the sample 12 at the proper imaging height, i.e., in the focal plane of the lens 38, is made easy and reliable by the use of alignment stops. Referring to FIG. 2, the imaging system includes three or four alignment stops 56 which are fixed relative to the imaging optics. The tips of the stops 56 are all disposed in the focal plane of the imaging lens 38. The sample 12 is supported on a sample slide 60, which is in turn mounted on a slide mount 62 fixed on the stage 14. The mounting surface of the slide mount 62 includes springs 66 for supporting the under side of the sample slide. To load the sample slide 60 on the slide mount 62, the stage 14 is lowered to provide clearance for placing the slide on the support springs 66 of the mount. The stage 14 is then moved up to a position where the upper surface of the sample slide 60 is in contact with the tips of the alignment stops 56 and the springs 66 are adequately compressed. At this position, the sample is in the focal plane of the lens 38 for imaging. The compressed springs 66 provide the biasing force for reliably holding the sample slide 60 against the tips of the alignment stops 56. Due to the use of spring loading on the slide mount, the slide mount does not have to be positioned precisely to achieve proper image focusing. The fixed positions of the alignment stops guarantees that the sample can be placed in the focal plane of the imaging lens 38 every time quickly and easily without the need for any sample height fine adjustments required in conventional focusing setups.

In view of the foregoing detailed description, it can be appreciated that the invention provides a large-field fluorescence imaging apparatus that is capable of providing high quality fluorescent images at a significantly improved imaging rate. The imaging apparatus achieves a high illumination intensity by employing a high-power white light source and using reflective optics to couple the excitation beam to the sample surface. The imaging efficiency is enhanced by the use of simple imaging optics and an array detector for parallel collection of the fluorescent light from the sample. In an implementation of the embodiment of FIG. 1 with a 175-watt xenon arc lamp as the light source, a high-quality fluorescent image of a sample with a field of view of 12.5 $cm^2$ is typically obtainable in about 2 seconds. The use of a white light source reduces the cost of the imaging apparatus and provides flexibility in the selection of the excitation frequency. The optical configuration of the invention also allows the imaging apparatus to have a compact, robust construction.

What is claimed is:

1. A large-field fluorescence imaging apparatus for acquiring a fluorescent image of a sample under study, comprising:
   a white light source coupled with a reflector for producing a collimated white light beam,
   an input filter for filtering the white light beam to produce an excitation beam having an excitation frequency band;
   an excitation input path between the input filter and the sample having a single reflective focusing element in the form of a concave mirror for projecting the excitation beam onto the sample for generating fluorescent light therein;
   an array detector for detecting the fluorescent light from the sample for generating a fluorescent image of the sample;
   imaging optics for imaging the fluorescent light from the sample onto the array detector; and
   an output filter disposed between the sample and the array detector for removing unwanted light while passing the fluorescent light from the sample.

2. A large-field fluorescence imaging apparatus as in claim 1, further including a field stop disposed to intercept the excitation beam to define a beam pattern, and wherein the concave mirror is disposed to image the field stop on the sample for defining an illumination area thereon.

3. A large-field fluorescence imaging apparatus as in claim 2, further including a plane mirror disposed between the field stop and the concave mirror for redirecting the excitation beam onto the concave mirror.

4. A large-field fluorescence imaging apparatus as in claim 1, wherein the concave mirror is a spherical mirror.

5. A large-field fluorescence imaging apparatus as in claim 1, wherein the array detector is a charge coupled device.

6. A large-field fluorescence imaging apparatus as in claim 1, wherein the imaging optics includes first and second imaging lenses disposed between the sample and the array detector.

7. A large-field fluorescence imaging apparatus as in claim 1, further including an infrared filter disposed between the white light source and the input filter for removing an infrared portion of the white light beam.

8. A large-field fluorescence imaging apparatus as in claim 1, further including alignment stops for defining an imaging height of the sample, the alignment stops each having an end disposed in a focal plane of the imaging optics for contacting a sample slide on which the sample is mounted to hold the sample in the focal plane during imaging operation.

9. A large-field fluorescence imaging apparatus for acquiring a fluorescent image of a sample under study, comprising:
   a white light source coupled with a reflector for producing a collimated white light beam,
   an input filter for filtering the white light beam to produce an excitation beam having an excitation frequency band;
   a concave mirror for projecting the excitation beam onto the sample for generating fluorescent light therein, wherein the concave mirror projects the excitation beam onto the sample at an acute incident angle;
   an array detector for detecting the fluorescent light from the sample for generating a fluorescent image of the sample;
   imaging optics for imaging the fluorescent light from the sample onto the array detector; and
   an output filter disposed between the sample and the array detector for removing unwanted light while passing the fluorescent light from the sample.

10. A large-field fluorescence imaging apparatus for acquiring a fluorescent image of a sample under study, comprising:
   a white light source coupled with a reflector for producing a collimated white light beam,
   an input filter for filtering the white light beam to produce an excitation beam having an excitation frequency band;
   a concave mirror for projecting the excitation beam onto the sample for generating fluorescent light therein;
   an array detector for detecting the fluorescent light from the sample for generating a fluorescent image of the sample;
   imaging optics for imaging the fluorescent light from the sample onto the array detector, including first and second imaging lenses disposed between the sample and the array detector; and
   an output filter disposed between the first and second imaging lenses for removing unwanted light while passing the fluorescent light from the sample.

11. A large-field fluorescence imaging apparatus for acquiring a fluorescent image of a sample under study, comprising:
   a white light source coupled with a reflector for producing a collimated white light beam;
   an input filter for filtering the white light beam to produce an excitation beam having an excitation frequency band, wherein the input filter is mounted on a filter wheel for supporting a plurality of filters which are selectable by rotating the filter wheel;
   a concave mirror for protecting the excitation beam onto the sample for generating fluorescent light therein;
   an array detector for detecting the fluorescent light from the sample for generating a fluorescent image of the sample;
   imaging optics for imaging the fluorescent light from the sample onto the array detector; and
   an output filter disposed between the sample and the array detector for removing unwanted light while passing the fluorescent light from the sample.

12. A large-field fluorescence imaging apparatus for acquiring a fluorescent image of a sample under study, comprising:
   a white light source coupled with a reflector for producing a collimated white light beam, an input filter for filtering the white light beam to produce an excitation beam having an excitation frequency band;
   a concave mirror for protecting the excitation beam onto the sample for generating fluorescent light therein;
   an array detector for detecting the fluorescent light from the sample for generating a fluorescent image of the sample;
   imaging optics for imaging the fluorescent light from the sample onto the array detector; and
   an output filter disposed between the sample and the array detector for removing unwanted light while passing the fluorescent light from the sample, wherein the output filter is mounted on a filter wheel for supporting a plurality of filters which are selectable by rotating the filter wheel.

13. A large-field fluorescence imaging apparatus as in claim 12, wherein the output filter has multiple fluorescent light pass bands.

14. A large-field fluorescence imaging apparatus for acquiring a fluorescent image of a sample mounted on a sample slide, comprising:
   a white light source coupled with a reflector for producing a collimated white light beam,
   an input filter for filtering the white light beam to produce an excitation beam having an excitation frequency band;
   a concave mirror for projecting the excitation beam onto the sample for generating fluorescent light therein,
   an array detector for detecting the fluorescent light from the sample for generating a fluorescent image of the sample;
   imaging optics for imaging the fluorescent light from the sample onto the array detector;
   an output filter disposed between the sample and the array detector for removing unwanted light while passing the fluorescent light from the sample; and
   a plurality of alignment stops each having an end disposed in a focal plane of the imaging optics for contacting with the sample slide to hold the sample in the focal plane for imaging.

15. A large-field fluorescence imaging apparatus as in claim 14, further including:
   a slide mount having springs for supporting the sample slide;
   a stage for supporting the slide mount, the stage being movable to move the slide mount into an imaging position where the sample slide is in contact with the ends of the alignment stops and the springs on the slide mount are compressed to hold the sample slide against the alignment stops.

16. A large-field fluorescence imaging apparatus as in claim 15, wherein the array detector is a charge coupled device.

17. A large-field fluorescence imaging apparatus as in claim 14, further including a field stop disposed between the input filter and the concave mirror for shaping the excitation beam, wherein the concave mirror is disposed to image the field stop on the sample to define an illumination area.

* * * * *